(12) United States Patent
Santangelo et al.

(10) Patent No.: US 9,517,062 B2
(45) Date of Patent: Dec. 13, 2016

(54) CLOSED LOOP SUTURE FOR ANCHORING TISSUE GRAFTS

(71) Applicant: Smith & Nephew, Inc., Memphis, TN (US)

(72) Inventors: Stephen Anthony Santangelo, Sturbridge, MA (US); Alfred Rodrigue Berube, Jr., North Attleboro, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/630,868

(22) Filed: Feb. 25, 2015

(65) Prior Publication Data

US 2016/0157861 A1      Jun. 9, 2016

Related U.S. Application Data

(60) Provisional application No. 62/086,991, filed on Dec. 3, 2014.

(51) Int. Cl.
| | |
|---|---|
| A61B 17/04 | (2006.01) |
| A61B 17/06 | (2006.01) |
| A61F 2/08 | (2006.01) |
| A61B 17/00 | (2006.01) |

(52) U.S. Cl.
CPC ..... *A61B 17/06166* (2013.01); *A61B 17/0401* (2013.01); *A61F 2/0811* (2013.01); *A61B 2017/00969* (2013.01); *A61B 2017/0404* (2013.01); *A61B 2017/06185* (2013.01); *A61F 2002/0852* (2013.01)

(58) Field of Classification Search
CPC ............... A61B 2017/06185; A61B 17/06166; A61B 17/0401; A61F 2/0811

USPC .......................................................... 606/228
See application file for complete search history.

(56) References Cited

U.S. PATENT DOCUMENTS

| | | | |
|---|---|---|---|
| 3,463,158 | A | 8/1969 | Schmitt et al. |
| 3,513,484 | A | 5/1970 | Hausner |
| 4,034,763 | A | 7/1977 | Frazier |
| 4,127,902 | A | 12/1978 | Homsy |
| 4,149,277 | A | 4/1979 | Bokros |
| 4,246,660 | A | 1/1981 | Wevers |

(Continued)

FOREIGN PATENT DOCUMENTS

| | | |
|---|---|---|
| CA | 2215943 A1 | 9/1996 |
| DE | 29607352 U1 | 12/1996 |

(Continued)

OTHER PUBLICATIONS

Smith & Nephew Endobutton Family of Fixation Devices, brochure, © 2012 Smith & Nephew, Inc.

(Continued)

*Primary Examiner* — Gregory Anderson
*Assistant Examiner* — Christina Lauer
(74) *Attorney, Agent, or Firm* — Fish & Richardson P.C.

(57) ABSTRACT

A method and device for securing a tissue graft within a bone passage includes providing a graft fixation device that houses a closed loop having both braided and non-braided portions. A tissue graft is looped through the closed loop at the non-braided portion to attach the tissue graft to the graft fixation device. The graft fixation device is passed through the bone passage and seated against the surface of the bone to secure the tissue graft within the bone passage.

16 Claims, 8 Drawing Sheets

(56) References Cited

U.S. PATENT DOCUMENTS

| | | |
|---|---|---|
| 4,610,688 A | 9/1986 | Silvestrini et al. |
| 4,668,233 A | 5/1987 | Seedhom et al. |
| 4,792,336 A | 12/1988 | Hlavacek et al. |
| 4,979,956 A | 12/1990 | Silvestrini |
| 4,997,434 A | 3/1991 | Seedhom et al. |
| 5,004,474 A | 4/1991 | Fronk et al. |
| 5,024,669 A | 6/1991 | Peterson et al. |
| 5,041,129 A | 8/1991 | Hayhurst et al. |
| 5,049,155 A | 9/1991 | Bruchman et al. |
| 5,139,520 A | 8/1992 | Rosenberg |
| 5,147,400 A | 9/1992 | Kaplan et al. |
| 5,152,790 A | 10/1992 | Rosenberg et al. |
| 5,197,983 A | 3/1993 | Berman et al. |
| 5,306,301 A | 4/1994 | Graf et al. |
| 5,318,575 A | 6/1994 | Chesterfield et al. |
| 5,571,104 A | 11/1996 | Li |
| 5,575,819 A | 11/1996 | Amis |
| 5,688,451 A | 11/1997 | Hutton |
| 5,769,894 A | 6/1998 | Ferragamo |
| 5,871,504 A | 2/1999 | Eaton et al. |
| 6,045,571 A * | 4/2000 | Hill .......... A61B 17/06166 606/228 |
| 6,174,324 B1 | 1/2001 | Egan et al. |
| 6,193,754 B1 | 2/2001 | Seedhom |
| 6,352,603 B1 | 3/2002 | Bryant |
| 6,398,807 B1 | 6/2002 | Chouinard et al. |
| 6,533,802 B2 | 3/2003 | Bojarski et al. |
| 6,585,758 B1 | 7/2003 | Chouinard et al. |
| 7,285,124 B2 | 10/2007 | Foerster |
| 7,500,983 B1 | 3/2009 | Kaiser et al. |
| 7,530,990 B2 | 5/2009 | Perriello et al. |
| 8,197,508 B2 | 6/2012 | Egan et al. |
| 8,323,338 B2 | 12/2012 | LeBeau et al. |
| 8,663,324 B2 | 3/2014 | Schmieding et al. |
| 8,881,635 B2 | 11/2014 | Martin |
| 2002/0173788 A1 | 11/2002 | Bojarski et al. |
| 2004/0267362 A1 | 12/2004 | Hwang et al. |
| 2007/0270857 A1 | 11/2007 | Lombardo et al. |
| 2008/0046009 A1* | 2/2008 | Albertorio .......... A61B 17/0401 606/232 |
| 2008/0234819 A1 | 9/2008 | Schmieding et al. |
| 2009/0018654 A1 | 1/2009 | Schmieding et al. |
| 2009/0275974 A1 | 11/2009 | Marchand et al. |
| 2010/0256677 A1 | 10/2010 | Albertorio et al. |
| 2010/0324676 A1 | 12/2010 | Albertorio et al. |
| 2011/0054524 A1 | 3/2011 | Beevers et al. |
| 2011/0087280 A1 | 4/2011 | Albertorio |
| 2011/0093055 A1 | 4/2011 | Kujawski |
| 2012/0123474 A1 | 5/2012 | Zajac |
| 2012/0123541 A1* | 5/2012 | Albertorio .......... A61B 17/0401 623/13.14 |
| 2012/0290002 A1* | 11/2012 | Astorino .......... A61B 17/0401 606/232 |
| 2013/0079778 A1* | 3/2013 | Azuero .......... A61F 2/0811 606/74 |
| 2013/0317544 A1 | 11/2013 | Ferguson et al. |
| 2014/0039620 A1 | 2/2014 | Cantournet et al. |
| 2014/0243976 A1 | 8/2014 | Schmieding et al. |
| 2014/0277122 A1 | 9/2014 | Johnson |
| 2015/0066081 A1 | 3/2015 | Martin |

FOREIGN PATENT DOCUMENTS

| | | |
|---|---|---|
| WO | WO9216167 A1 | 10/1992 |
| WO | WO9620648 A1 | 7/1996 |
| WO | WO9629029 A1 | 9/1996 |

OTHER PUBLICATIONS

Ochi, M., et al., "Looped Artificial Ligament Developed for Reconstruction of Anterior Cruciate Ligament of the Knee," The Knee, vol. 22, 1996, pp. 92-94.

Mochizuki, Y., et al., "The Arthroscopic Reconstruction of Anterior Cruciate Ligament using EndoButton—procedure and pittfalls-," Journal of Tokyo Knee Society, vol. 17, 1996.

Ochi, M., et al., "Kojujijintaisonsho," OS Now Orthopaedic Surgery, No. 23, pp. 62-71, with English-language translation of the descriptions of Figs. 10 and 11, 1996.

International Search Report and Written Opinion for International Application No. PCT/US2015/063670, issued Mar. 2, 2016.

* cited by examiner

CLOSED LOOP SUTURE FOR ANCHORING TISSUE GRAFTS

TECHNICAL FIELD

This invention relates to closed loop suture for anchoring tissue grafts.

BACKGROUND

An increasing number of surgical techniques are now performed arthroscopically. One type of arthroscopic procedure reconstructs the anterior cruciate ligament (ACL) in the knee. Several ACL reconstruction techniques are described in U.S. Pat. Nos. 5,139,520, 5,306,301, and 5,769,894, incorporated herein by reference in their entirety.

When the ACL has ruptured and is nonrepairable, it can be replaced using a substitute graft harvested from the patient or from a donor. The substitute ACL graft may be a portion of a patellar tendon or a semitendinosus and/or gracilis tendon graft. Alternatively, an artificial graft formed from synthetic materials or from a combination of artificial and natural materials may be used and is sometimes referred to as a ligament augmentation device (LAD). The term "tissue graft" is used herein to encompass all of these tissue replacements.

In general, the replacement tissue graft is placed within a passage formed within the femur and a passage formed in the tibia, and secured to the femur and tibia.

SUMMARY

In one aspect, the invention features a suture loop comprising a braided length of filaments and a non-braided length of the filaments, where the braided length of the filaments and the non-braided length of the filaments form the loop.

One or more of the following features may also be included. The filaments are in the form of yarns, each yarn including multiple filaments. The braided length of the filaments comprises braided yarn. The non-braided length of the filaments comprises yarn twisted together. The yarns comprise monofilaments twisted together. The yarns comprise air-entangled monofilaments. Each yarn has a minimum denier of 198 and comprises monofilaments. The braided length of the filaments comprises a first section of braided filaments and a second section of braided filaments, and the non-braided length of the filaments is located between the first and second sections, wherein the first and second sections connect to form the suture loop. The second section defines a hollow conduit and a portion of the first section is inside the conduit to form the suture loop. The suture loop comprises at least one stitch securing the connection between the first and second sections of the braided filaments.

In another aspect, the invention features a method of manufacturing a suture loop. The method comprises connecting a first braided length of suture and a second braided length of suture to form the suture loop, the suture loop including a non-braided length of suture.

One or more of the following features may also be included. The method comprises threading the first braided length of suture through a button of a fixation device before connecting the first braided length of suture and the second braided length of suture to form the suture loop. Connecting the first braided length of suture and the second braided length of suture to form the suture loop comprises inserting the first braided length of suture into a hollow interior of the second braided length of suture. The method comprises stitching the connection between the first braided length of suture and the second braided length of suture. The method comprises before connecting the first braided length of suture and the second braided length of suture to form the suture loop, twisting the non-braided length of suture.

In another aspect, the invention features a method for securing a tissue graft within a bone passage. The method comprises forming a bone passage in a bone to accommodate the tissue graft. The method comprises coupling the tissue graft to a loop of suture, the loop of suture comprising a braided length of filaments and a non-braided length of the filaments. The tissue graft is positioned within the bone passage, and the tissue graft is secured in the bone passage.

One or more of the following features may also be included. The loop of suture is part of a fixation device and securing the tissue graft comprises placing a button of the fixation device across an opening of the bone passage. Positioning the tissue graft comprises pulling a filament attached to the button of the fixation device. The bone passage is formed in a femur.

In another aspect, a surgical device for securing a tissue graft within a bone passage comprises an elongated body and a loop of suture housed by the elongated body, wherein the loop of suture comprises a braided portion and a non-braided portion.

One or more of the following features may also be included. The elongated body defines a hole that receives a loop of suture. The elongated body defines a first hole and a second hole that receive the loop of suture. The elongated body defines a third hole and a fourth hole. A leading filament and a trailing filament are each received by one of the third and fourth holes. The first hole and the second hole are positioned centrally, the third hole is positioned on one side of the first and second holes and the fourth hole is positioned on an opposite side of the first and second holes.

Embodiments have one or more of the following advantages. The closed loop having both braided lengths of filaments and non-braided lengths of filaments provides added strength at the braided portions of the loop, and added compliance and improved wear at the non-braided portions of the loop. Fixing the braided portion of the loop to the graft fixation device strengthens the junction between the loop and the graft fixation device. Similarly, fixing the non-braided portion of the loop to the tissue graft allows for a more reliable junction with the tissue graft. The closed loop having both braided and non-braided lengths provides superior strength over loops that are tied or taped, or that do not feature both braided and non-braided portions. Moreover, the closed loop having both braided and non-braided lengths of filaments allows for added flexibility in the manufacturing of closed loop sutures, as the sutures can be manufactured independently of the graft fixation device and at varying lengths as required by the specific application.

The details of one or more embodiments of the invention are set forth in the accompanying drawings and the description below. Other features, objects, and advantages of the invention will be apparent from the description and the drawings, and from the claims.

DETAILED DESCRIPTION

Figure 1:
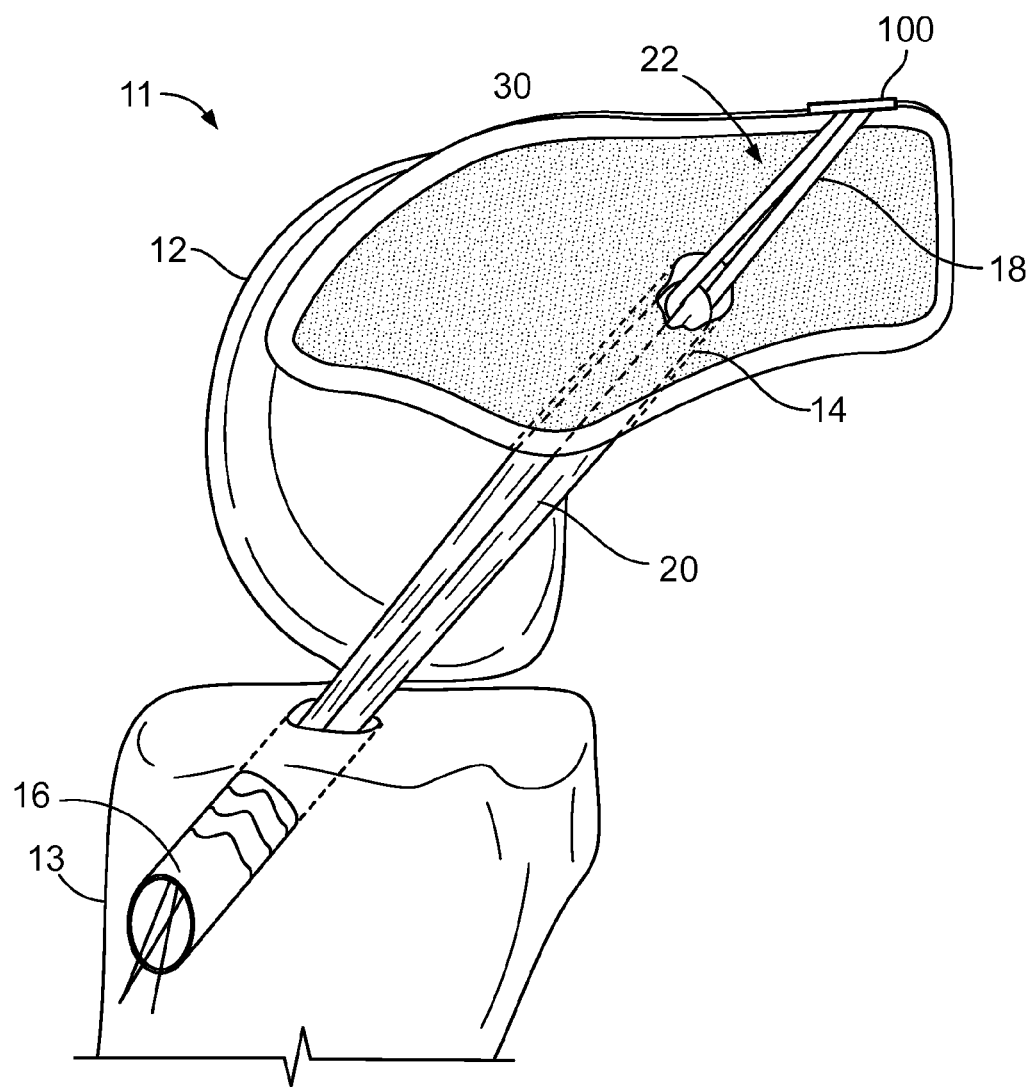
FIG. 1 shows an example of a tissue graft implanted in a knee during an ACL reconstruction procedure and secured at one end by a graft fixation device including a closed loop suture.
Figure 2:
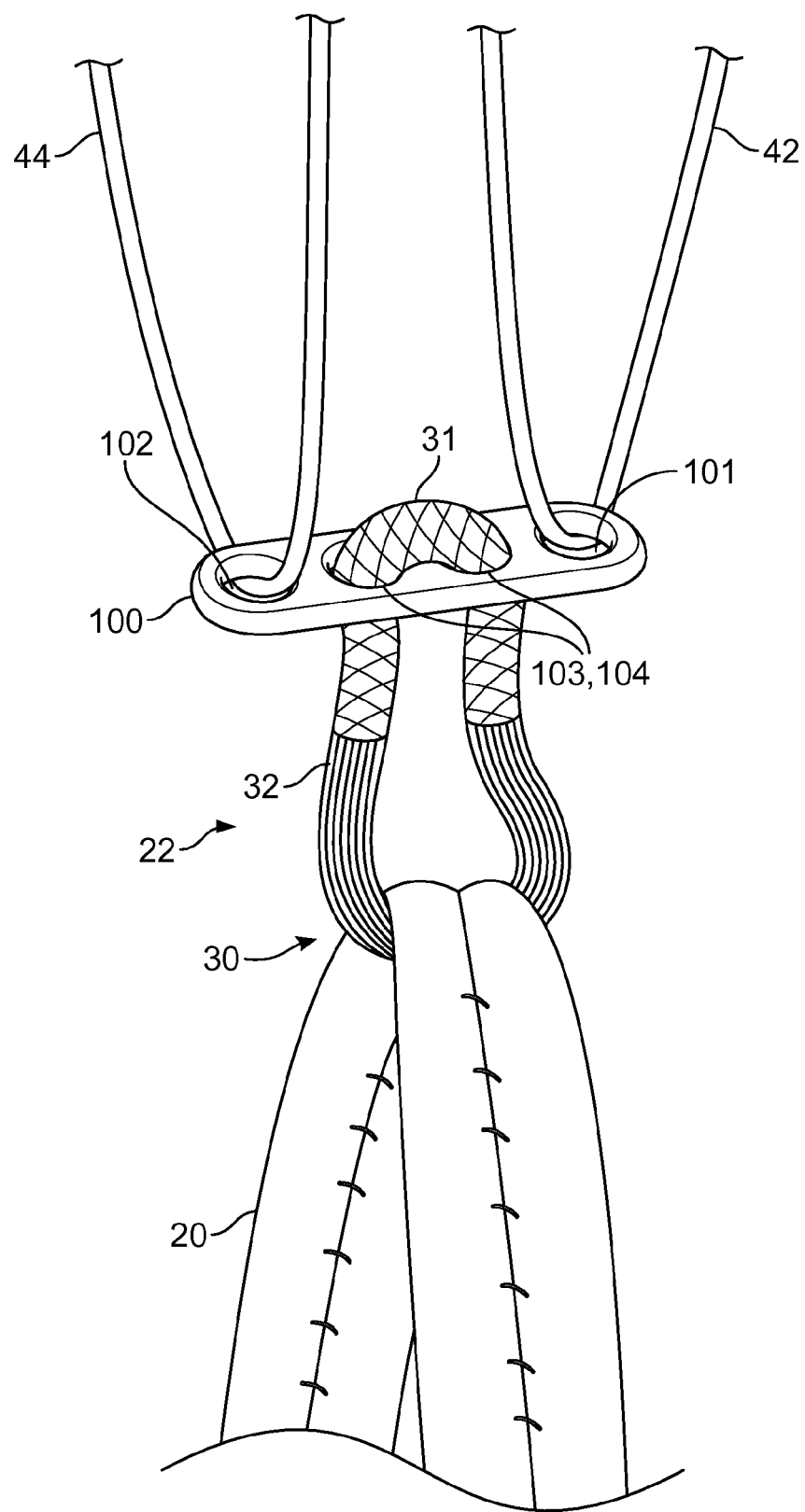
FIG. 2 shows the tissue graft and the graft fixation device.

Referring to FIG. 1, a tissue graft 20 is shown implanted within a knee 11 during an anterior cruciate ligament (ACL) repair and reconstruction procedure. The tissue graft 20 is sized to fit within a femoral channel 14 formed in a femur 12 and a tibial channel 16 formed in a tibia 13. The tissue graft 20 is secured to the femur 12 using a graft fixation device 22, and is secured to the tibia 13 using a fastener 24 (for example, an interference screw, a post, or another fixation device 22). The graft fixation device 22 includes a button 100, for example, an Endobutton available from Smith & Nephew (Catalog Number: 013186), and a closed-loop suture 30. Referring also to FIG. 2, the tissue graft 20 is attached to the graft fixation device 22 by looping the tissue graft through the closed-loop suture 30.

Figure 3:
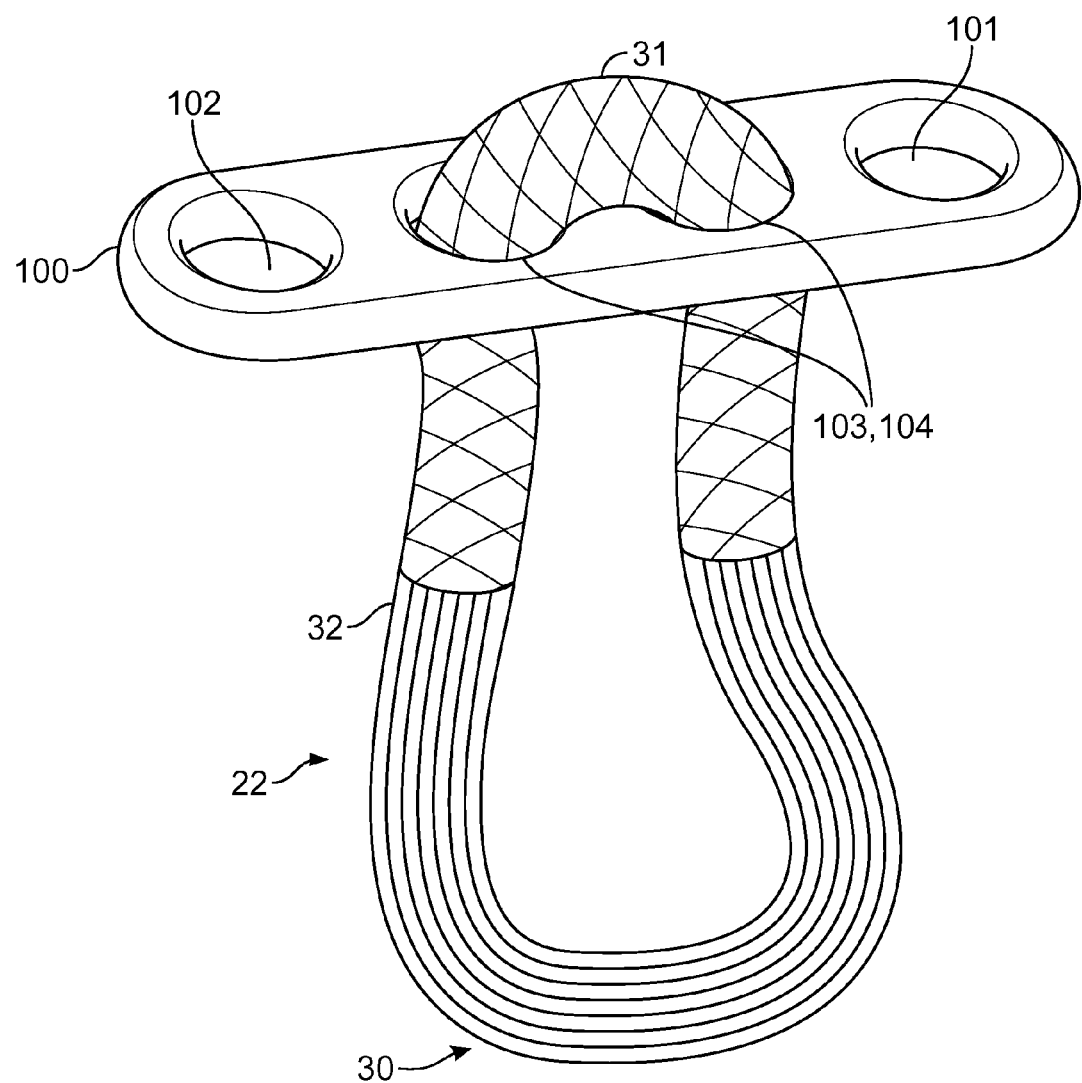
FIG. 3 shows the graft fixation device including the closed loop suture.
Figure 4:
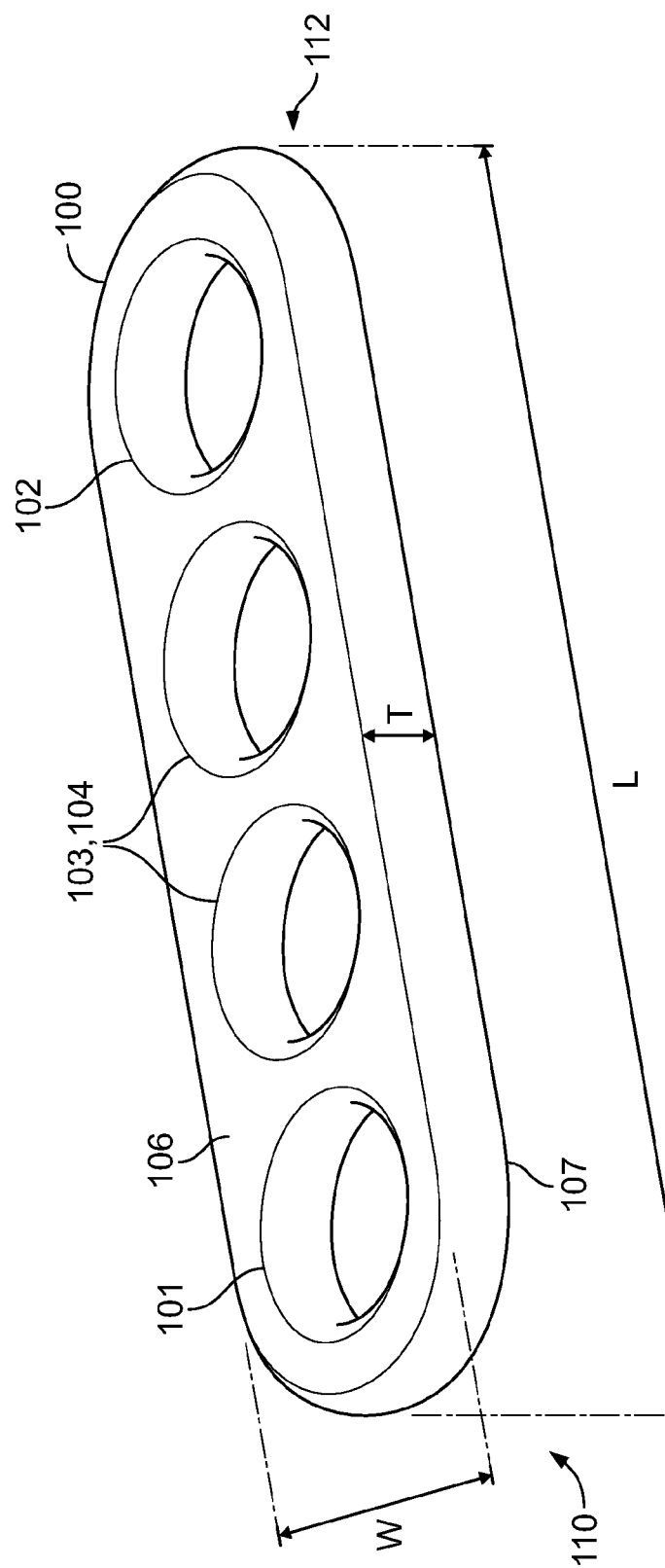
FIG. 4 is an isometric view of a button of the graft fixation device.

Referring to FIGS. 2-4, the button 100 has an elongated body with a top surface 106, a bottom surface 107, and ends 110, 112, and has a width, W, a length, L, and a thickness, T. The button 100 defines two central holes 103, 104, a leading end hole 101, and a trailing end hole 102 that pass through the button thickness, T. The central holes 103, 104 of the button 100 house the closed loop suture 30, which passes through the hole 103 from the bottom surface 107 of the button 100 to the top surface 106 of the button 100, over the top surface 106 of the button 100, and through the hole 104 from the top surface 106 of the button 100 to the bottom surface 107 of the button 100.

As described in further detail below, the closed loop suture 30 is a hybrid construct including a braided portion 31 of filaments located within the holes 103, 104 and passing over the top surface 106 of button 100, and a non-braided section 32 of the filaments located under the bottom surface 107 of the button 100. In some implementations, the braided portion 31 of filaments can extend below the holes 103, 104 and bottom surface 107 of the button 100, as shown at FIGS. 2 and 3. The tissue graft 20 is looped through the closed loop suture 30 such that the tissue graft 20 is positioned against the non-braided section 32. Such a configuration allows the stronger, braided length 31 of the closed loop suture 30 to form the connection to the button 100, which is desirable for reliability purposes. The more compliant and less abrasive non-braided section 32 of the closed loop suture 30 forms the connection to the tissue graft 20, which is desirable for pliability and to reduce wear on the tissue graft 20. As described above, the tissue graft 20 may be a portion of a patellar tendon, semitendinosus and/or gracilis tendon graft, an artificial graft formed from synthetic materials, or a hybrid tissue graft formed from a combination of artificial and natural materials.

As illustrated in FIG. 2, the leading end hole 101 houses a leading suture 42 for pulling the graft fixation device 22 and the tissue graft 20 through the bone passages. The leading suture 42 can be any suitable suture, for example, Smith & Nephew Size 5 ULTRABRAID™. The trailing end hole 102 houses a trailing suture 44 that can be used to manipulate the button 100. Similar to the leading suture 42, the trailing suture 44 can be any suitable suture, for example, Smith & Nephew Size 2 ULTRABRAID™.

Figure 5:
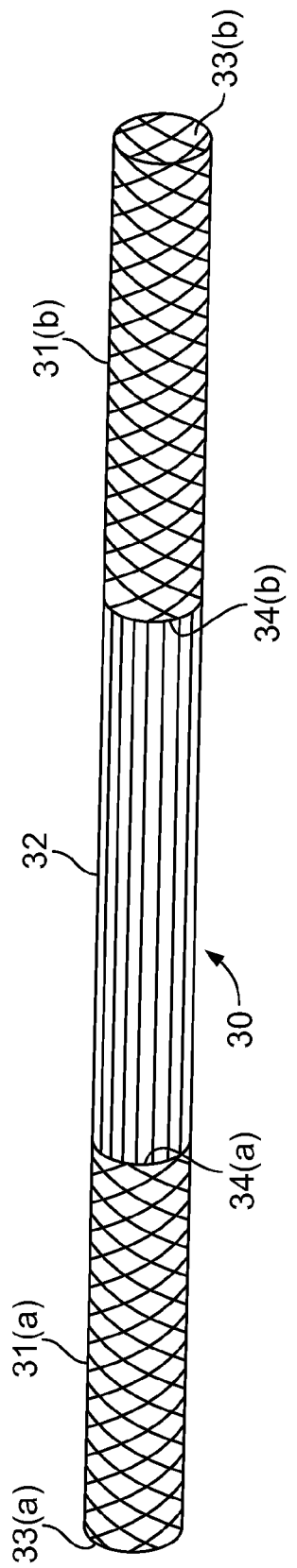
FIG. 5 depicts an example process for forming the closed loop suture.

As shown in FIG. 5, the closed loop suture 30 is formed, for example, from a continuous length of suture having two braided end sections 31a, 31b and a non-braided section 32 therebetween. The braided end sections 31a, 31b are tubular with hollow interiors. For example, the braided end sections 31a, 31b may be of a form similar to Smith & Nephew Size 2 ULTRABRAID™ (Catalog Number 90505373). To form the closed loop, the two braided end sections 31a, 31b are connected. Each of the braided end sections 31a, 31b has a respective end 33a, 33b. The braided end sections 31a, 31b are connected, for example, by inserting the end 33b of the braided end section 31b into the hollow conduit of the braided end section 31a. To facilitate the insertion of the braided end section 31b into the hollow conduit of the braided end section 31a, the diameter of the braided end section 31a can be increased by compressing the section 31a along its length. The diameter of the other braided end section 31b can be decreased by stretching the braided end section 31b along its length. The braided end section 31b is then inserted into the hollow conduit of the braided end section 31a. The braided end sections 31a, 31b are then allowed to return to their original lengths, such that the diameters of both braided end sections 31a, 31b return to their original dimensions forming a "finger trap" connection between the two braided end sections 31a, 31b, thereby completing the closed loop suture 30.

In some implementations, the length of the overlap between the braided end sections 31a, 31b can be adjusted to increase or decrease the strength of the "finger trap" connection. Since the "finger trap" connection relies on friction between the overlapping braided end sections 31a, 31b to complete the closed loop suture 30, a longer overlap increases the strength of the connection. Additionally or alternatively, the connection between the braided end sections 31a, 31b can be formed or reinforced using at least one stitch at a seam 35 or at one or more other locations along the length of the overlap between the braided end sections 31a, 31b. In other examples, the braided end sections 31a, 31b can be connected to form the closed loop suture 30 by other means, for example, by tying, gluing, stapling, or otherwise fixing the end sections together.

Figure 6:
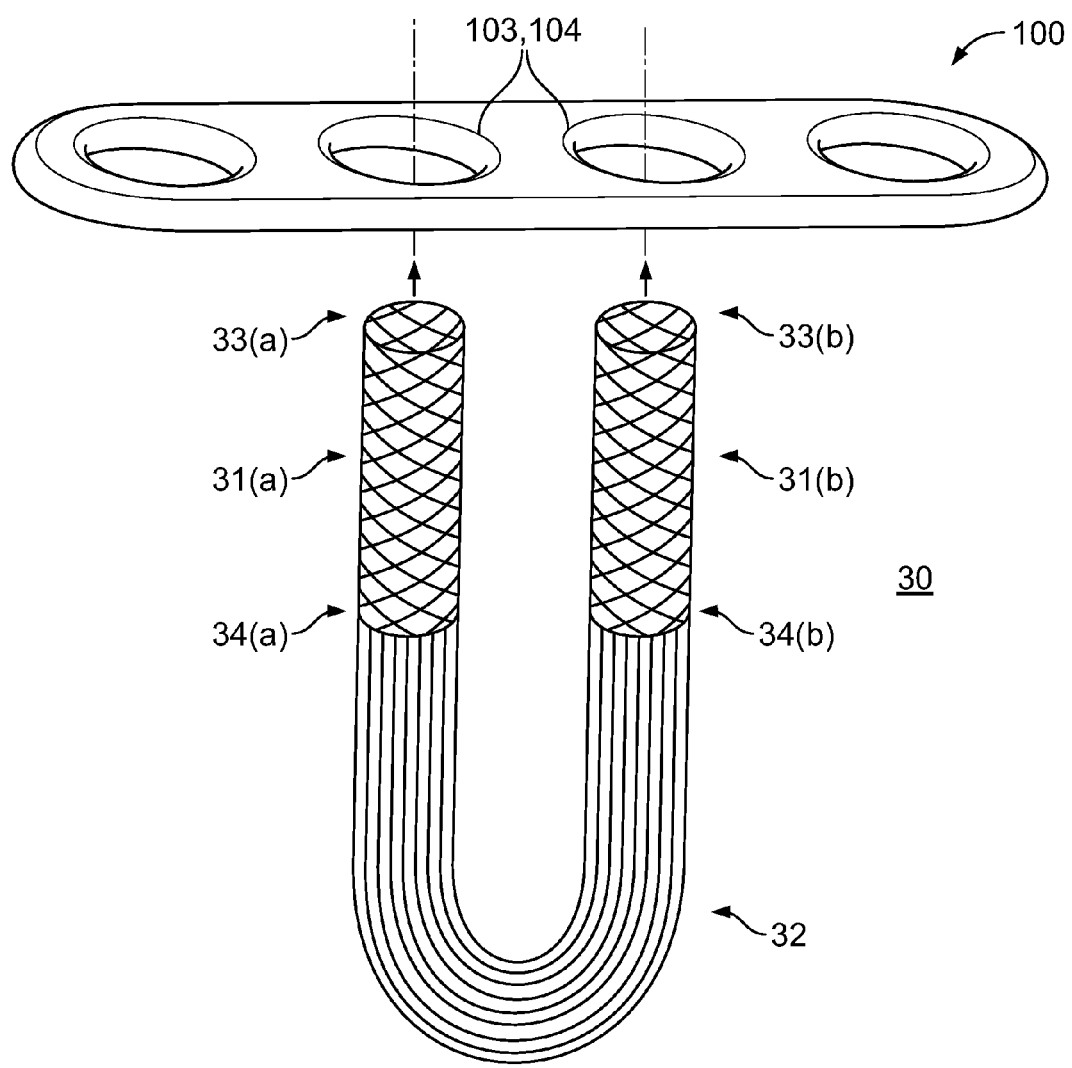
FIG. 6 depicts an example process for forming the closed loop suture on the button of the graft fixation device.

Referring to FIGS. 3 and 6, a closed loop suture 30 can be formed on a button 100 by threading each of the ends 33a, 33b through one of the central holes 103, 104 of the button 100. Once the braided end sections 31a, 31b are threaded through the central holes 103, 104 of the button 100, the braided end sections 31a, 31b are connected as discussed above with respect to FIG. 5 to form the closed loop suture 30.

The button 100 is formed, for example, of a biocompatible material (such as titanium or PEEK), or a bioabsorbable material (such as polylactic acid, polyglycolic acid or a combination of absorbable polymers). The body of the graft fixation device 100 is sized such that the graft fixation device 100 can be pulled through the tibial channel 16, the femoral channel 14, and a passing channel 18 (FIG. 1). Furthermore, the body of the graft fixation device 100 is sized such that once the graft fixation device 100 has been passed through each of the tibial channel 16, the femoral channel 14, and the passing channel 18, the graft fixation device can be seated against the surface of the femur 12 to secure the tissue graft 20 within the bone passages 14, 16, 18.

The four holes 101-104 may be distributed equally along the length of the button 100, as shown in FIG. 4, or may be distributed in other ways along the graft fixation device 100. In some implementations, each of the surfaces of the graft fixation device 100 are rounded, such that the body of the graft fixation device 100 is smooth and without sharp edges or angles.

The closed loop suture 30 is comprised of monofilament fibers that form the braided end sections 31*a*, 31*b* and the non-braided section 32. In some instances, the braided end sections 31*a*, 31*b* and non-braided section 32 (FIG. 5) can be manufactured, for example, using standard commercial braiding machinery, such as that described in U.S. Pat. No. 8,881,635, hereby incorporated by reference in its entirety. The braiding machine may be equipped with multiple spools of yarn that are each loaded on one of multiple carriers of the braiding machine. The yarn may be formed from twisted together monofilament fibers or air-entangled monofilament fibers, where the particular monofilaments used to form a particular yarn may be dependent upon the application. For example, yarns used to form the closed loop suture 30 may comprise monofilament fibers, where the yarns have a minimum denier of 198, to a maximum denier of 792. A braiding machine having at least 8 carriers, and up to 16 carriers, may be used to form the braided end sections 31*a*, 31*b* and non-braided section 32 of the closed loop suture 30, where each carrier is equipped with at least one yarn. In some instances, multiple yarns may be loaded on a single carrier of a braiding machine to achieve a desired result. For example, a braiding machine having 12 carriers may be equipped with 2 yarns per carrier to achieve a desired braid strength or density, such as a braid having a linear mass density of 375 denier. Other configurations may be used depending upon the particular application or the capabilities of a particular braiding machine. The process of forming the closed loop suture 30 includes, for example, braiding the first end section 31*a* using the braiding machine, stopping the braiding machine from braiding, while the braiding machine is stopped, pulling the multifilament yarns that are loaded on the carriers of the braiding machine through the braiding machine to form the non-braided portion 32 of the closed loop suture 30, and then again braiding the yarns to form the second end section 32*b* using the braiding machine, as described in U.S. Pat. No. 5,147,400, which is hereby incorporated by reference in its entirety. By following this process, the resulting closed loop suture 30 comprising the braided end sections 31*a*, 31*b* and the non-braided section 32 is formed from continuous monofilament fibers.

In one example, the first braided end section 31*a* of braided suture and the second braided end section 31*b* of braided suture can have similar dimensions, including a similar length, a similar outer diameter defined by the outer portion of the tubular braid, and a similar inner diameter, defined by the hollow conduit of the inner portion of the tubular braid.

In some instances the braided length 31 of the closed loop suture 30 and the non-braided length of the closed loop suture 30 can also have similar dimensions. For example, a closed loop suture 30 with a circumference of 20 mm can include a non-braided portion 32 that is 10 mm in length, and a braided portion that is also 10 mm in length, such that each of the sections 31*a*, 31*b* is more than 5 mm in length to allow for the overlapping of the sections 31*a*, 31*b* to form the "finger trap" connection between the two braided ends 31*a*, 31*b*. In some examples, the length of the non-braided portion 32 is equal to, more, or less than half of the loop diameter. In some examples, the non-braided portion 32 is twisted, where twisting the non-braided length of suture 32 can increase the uniformity and deter fraying of the non-braided portion 32 of suture. For example, the non-braided portion 32 can be twisted one half rotation to deter fraying of the non-braided portion 32 of suture. The non-braided portion 32 may be twisted by other amounts, for example, by twisting the non-braided portion 32 a full rotation or multiple rotations.

Figure 7:
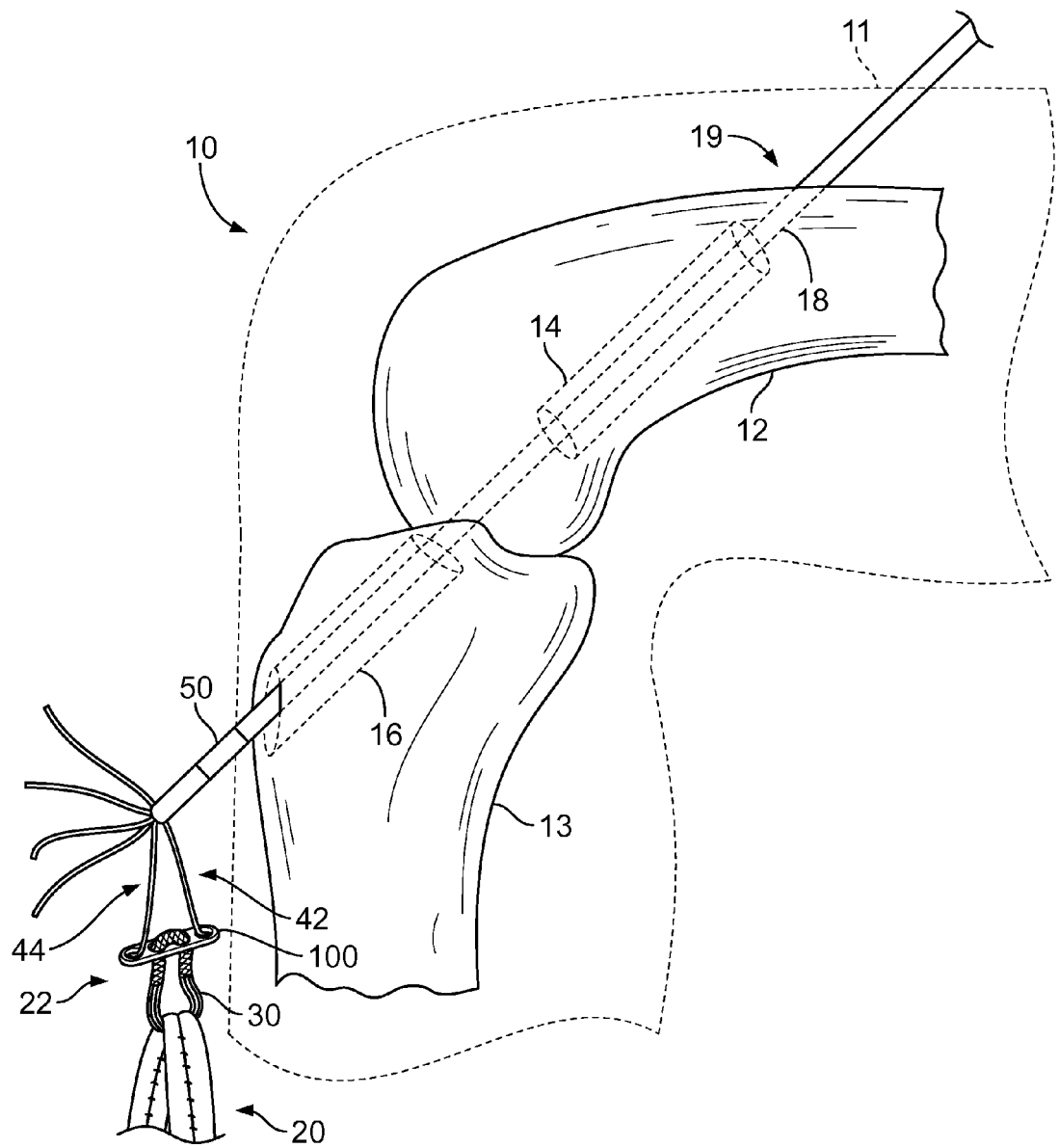
FIG. 7 shows the tissue graft being implanted during an ACL reconstruction procedure.
Figure 8A:
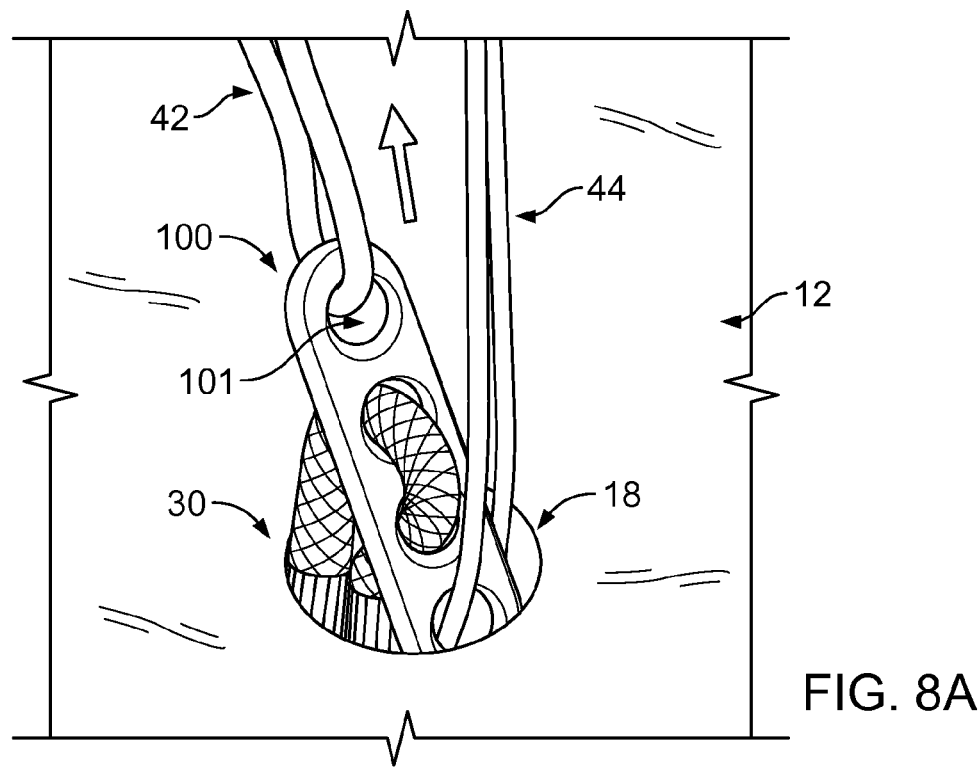
FIGS. 8A and 8B depict a process for seating the button of the graft fixation device against a bone to secure the tissue graft.
Figure 8B:
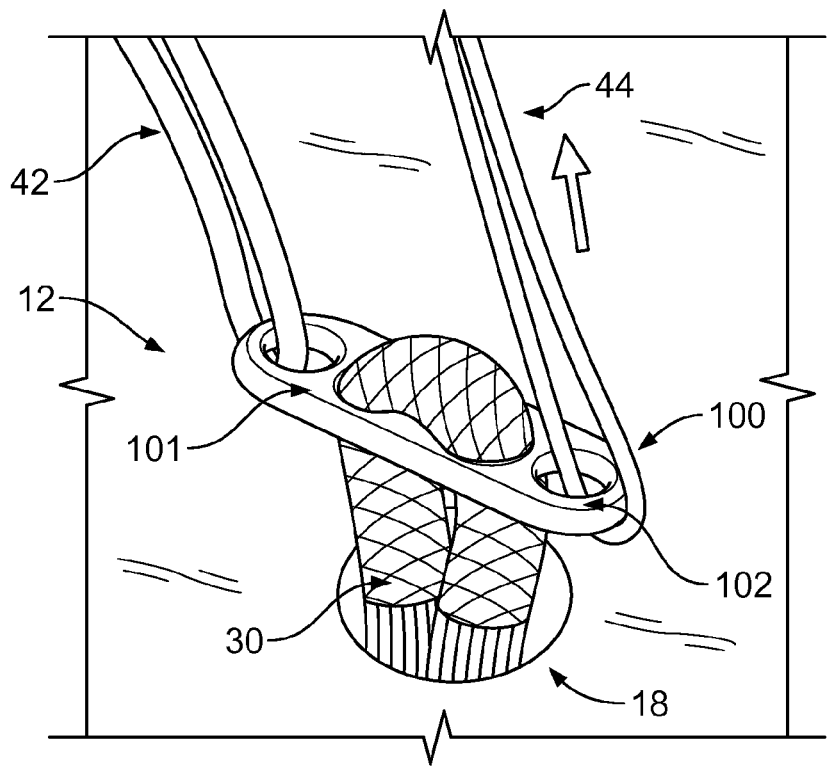

FIG. 7 shows the tissue graft 20 being implanted during the ACL repair and reconstruction procedure using the graft fixation device 22. The procedure begins by drilling the appropriately sized tibial channel 16, the appropriately sized femoral channel 14, and the appropriately sized passing channel 18. The leading filament 42 and trailing filament 44 are removably attached to a passing pin 50. The leading filament may function as a pulling suture used to draw the graft fixation device 22 that is attached to the tissue graft 20 through the bone channels 14, 16. The passing pin 50 is inserted through an incision below the knee and advanced through tibial channel 16, femoral channel 14, and passing channel 18, the quadriceps muscle surrounding the femur 12, and the skin of the knee 11. Ends of the leading filament 42 and trailing filament 44 are withdrawn beyond the skin of the knee 11 using the passing pin 50. A surgeon can pull the graft fixation device 22 that is attached to the tissue graft 20 through the tibial channel 16, femoral channel 14, and passing channel 18 by pulling predominantly on the leading filament 42. Once the button 100 emerges from the passing channel 18 (FIG. 8A), the surgeon positions the button 100 transversely to the passing channel 18 and across the opening 19 of the passing channel 18 by pulling predominantly on the trailing filament 44, as illustrated in FIG. 8B. In this way, the trailing filament 44 acts as a flipping suture to rotate the button 100 transverse to the passing channel 18. The surgeon can then proceed to seat the graft fixation device against the surface of the femur 12, tension the tissue graft 20, and secure the tissue graft 20 within the femoral channel 14 and the tibial channel 16 by attaching the tissue graft 20 to the tibia 13 using, for example, an interference screw, a post, or another fixation device 22.

The graft fixation device can include a closed loop suture 30 formed in a double loop and used with a bone-tendon-bone tissue graft, as described, for example, in U.S. Pat. No. 7,530,990, hereby incorporated by reference in its entirety.

In general, the graft fixation device 22 can be used to secure any suitable kind of graft, such as allografts, autografts, and xenografts and can be used in surgical soft tissue reconstruction procedures other than those related to ACL repair and reconstruction. For example, the graft fixation device 22 can be used for the fixation of tendons and ligaments during other orthopedic reconstruction procedures such as posterior cruciate ligament (PCL) repair and reconstruction, biceps tenodesis, distal biceps, and small joint procedures.

The closed loop suture 30 can be assembled independently of the button 100 using the techniques discussed with respect to FIG. 5.

What is claimed is:
1. A suture loop comprising:
   a tubular braided length of filaments, the braided length of filaments defining a hollow conduit; and
   a non-braided length of filaments, where the braided length of filaments and the non-braided length of filaments form the suture loop, wherein filaments that are braided to define the hollow conduit are not braided to form the non-braided length of filaments.

2. The suture loop of claim 1, wherein the filaments of the tubular braided length of filaments and the filaments of the non-braided length of filaments are in the form of yarns, each yarn including multiple filaments.

3. The suture loop of claim 2, wherein the braided length of filaments comprises braided yarn.

4. The suture loop of claim 2, wherein the non-braided length of filaments comprises yarn twisted together.

5. The suture loop of claim 2, wherein the yarns comprise monofilaments twisted together.

6. The suture loop of claim 2, wherein the yarns comprise air-entangled monofilaments.

7. The suture loop of claim 2, wherein each yarn has a minimum denier of 198 and comprises monofilaments.

8. The suture loop of claim 1, wherein the braided length of filaments comprises a first section of braided filaments and a second section of braided filaments, and the non-braided length of filaments is located between the first and second sections, wherein the first and second sections each have a terminal end, and the first and second sections connect to form the suture loop.

9. The suture loop of claim 8, wherein the second section defines a hollow conduit and a portion of the first section is inside the conduit to form the suture loop.

10. The suture loop of claim 8, comprising at least one stitch securing the connection between the first and second sections.

11. A surgical device for securing a tissue graft within a bone passage comprising:

an elongated body; and a loop of suture housed by the elongated body, wherein the loop of suture comprises a tubular braided length of filaments, the braided length of filaments defining a hollow conduit, and a non-braided length of filaments, wherein filaments that are braided to define the hollow conduit are not braided to form the non-braided length of filaments.

12. The surgical device of claim 11, wherein the elongated body defines a hole that receives the loop of suture.

13. The surgical device of claim 11, wherein the elongated body defines a first hole and a second hole that receive the loop of suture.

14. The surgical device of claim 13, wherein the elongated body defines a third hole and a fourth hole.

15. The surgical device of claim 14, including a leading filament and a trailing filament each received by one of the third and fourth holes.

16. The surgical device of claim 14, wherein the first hole and the second hole are positioned centrally, the third hole is positioned on one side of the first and second holes and the fourth hole is positioned on an opposite side of the first and second holes.

* * * * *